United States Patent [19]

Forssmann et al.

[11] Patent Number: 4,685,461
[45] Date of Patent: Aug. 11, 1987

[54] APPARATUS AND METHOD FOR TRIGGERING SHOCK WAVES IN LITHOTRIPSY

[75] Inventors: Bernd Forssmann, Friedrichshafen; Wolfgang Hepp, Immenstaad; Klaus Ackern, Gauting; Christian Chaussy, Germering, all of Fed. Rep. of Germany

[73] Assignee: Dornier System GmbH, Friedrichshafen, Fed. Rep. of Germany

[21] Appl. No.: 894,739

[22] Filed: Aug. 11, 1986

Related U.S. Application Data

[63] Continuation of Ser. No. 722,126, Apr. 10, 1985, abandoned, which is a continuation of Ser. No. 443,567, Nov. 22, 1982, abandoned.

[30] Foreign Application Priority Data

Nov. 25, 1981 [DE] Fed. Rep. of Germany ..... 31466281

[51] Int. Cl.⁴ ............................................. A61B 17/27
[52] U.S. Cl. .................................................. 128/328
[58] Field of Search ................ 128/328, 303 R, 303.1, 128/303.13–303.15, 303.17, 303.18, 699, 696, 419 R, 421, 671, 24 A

[56] References Cited

U.S. PATENT DOCUMENTS

| | | | |
|---|---|---|---|
| 3,129,704 | 4/1964 | Burt, Jr. ......................... | 128/419 R |
| 3,532,089 | 10/1970 | Arntzenius . | |
| 3,566,876 | 3/1971 | Stoft et al. ........................... | 128/421 |
| 3,572,317 | 3/1971 | Wade ..................................... | 128/671 |
| 3,835,845 | 9/1974 | Maher . | |
| 3,942,531 | 3/1976 | Hoff et al. . | |
| 3,970,076 | 7/1976 | Hepp et al. . | |
| 4,031,884 | 6/1977 | Henzel ............................... | 128/671 |
| 4,191,189 | 3/1980 | Barkan . | |
| 4,289,142 | 9/1981 | Kearns . | |
| 4,453,547 | 6/1984 | Castel et al. ........................ | 128/421 |

FOREIGN PATENT DOCUMENTS

| | | |
|---|---|---|
| 1039815 | 10/1978 | Canada . |
| 856788 | 11/1952 | Fed. Rep. of Germany . |
| 2635635 | 2/1978 | Fed. Rep. of Germany . |
| 2648282 | 4/1978 | Fed. Rep. of Germany ...... 128/695 |
| 446610 | 11/1967 | Switzerland . |
| 1436032 | 5/1976 | United Kingdom . |

OTHER PUBLICATIONS

D. Heyden in "Electronique Applications No. 5", pp. 5–8.
D. W. Hill and A. M. Dolan in "Intensive Care Instrumentation", pp. 213–216.
"Stosswellen in der Medizin", Medizin in unserer Zeit/4 Jahrg, 1980/Nr. 1.
"Der Internist", Heft 7, 1968, Seiten 314 bis 323, Aufsatz, Elektrotherapie kardialer Ryhthmusstorungen, von G. Rodewald et al.
"Kompendium Elektromedizin", 1. Auflage, 1976, Seiten 126 bis 131, Herausgeber: Siemens AG.
Zeithschrift "Rontgenstrahlen", Heft 32, 1975, Seiten 4 bis 10, Aufsatz, Herz- und atemphasengesteuerte Thoraxaufnahmen bei Kindern, von Ch. Dohlemann et al.
"The Servo Ventilator Concept", 1977, Produktprospekt der Fa. Siemens-Elema, insbesondere Seite 8, Zweite Spalte, erster Absatz.

*Primary Examiner*—Lee S. Cohen
*Attorney, Agent, or Firm*—Burns, Doane, Swecker & Mathis

[57] ABSTRACT

A trigger instrument for therapeutic shock waves, in particular for comminuting kidney stones, in which the shock waves are triggered by the R pip of the EKG or by a preselected time-delay thereafter.

8 Claims, 3 Drawing Figures

APPARATUS AND METHOD FOR TRIGGERING SHOCK WAVES IN LITHOTRIPSY

This application is a continuation of application Ser. No. 722,126, filed Apr. 10, 1985, now abandoned, which in turn is a continuation of application Ser. No. 443,567, filed on Nov. 22, 1982, now abandoned.

The invention relates to a trigger for therapeutic shock waves, for instance for comminuting kidney stones.

An instrument for the contactless comminution on concretions in bodies of living tissue by means of shock waves is known (note U.S. Pat. No. 3,942,531). In this instrument, electric discharges along a submerged spark gap generate shock waves in a focusing chamber, outside the body, the shock waves being focused on the concretion and comminuting it. These shock waves pass through the body tissue without damaging it. However, extrasystoles may be triggered in the stimulative phase of he heartbeat. Accordingly, the heart rhythm can be disturbed in patients with circulatory problems. In that case adequate circulation of the blood no longer will be ensured. Moreover, care must be taken when selecting the trigger time that the coordinates of the target, for instance the kidney—which are periodically changing due to breathing—shall be as constant as possible at the time of the shock wave triggering in order to achieve a high impact probability.

It is an object of the present invention to provide an instrument correlating the trigger time of the shock wave to the heart action in such a manner that the heart rhythm cannot be disturbed.

This problem is solved by the invention by an instrument triggering the shock wave by the QRS peak of the EKG, or by triggering with a selective time-delay thereafter.

Another object of the invention is to correlate the trigger time of the shock waves with the patient's breathing cycle, so that the focus point for the shock waves may be related more precisely to the particular location within the patient's body where shock wave impact is desired, such as at the location of a stone to be comminuted. This object may be realized by sensing the patient's breathing cycle (as with a spirometer or respirometer) and using the sensed signal for enabling generation of shock waves only during a selected portion of the patient's breathing cycle, such for example, as during the pause that follows exhalation. This feature may be used in conjunction with or separately from the feature by which shock wave triggering is correlated with the patient's heart rhythm.

One of the advantages of this invention is that shock waves can be applied to patients with impaired blood circulation and that this group of patients also can be spared surgical intervention. The physician is relieved, by the automatic time correlation with the heartbeat or further body functions, from the task of matching the shock wave application of the body rhythms. This permits avoidance of erroneous steps.

The invention will be further illustrated by reference to the accompanying drawings, in which.

Figure 1:
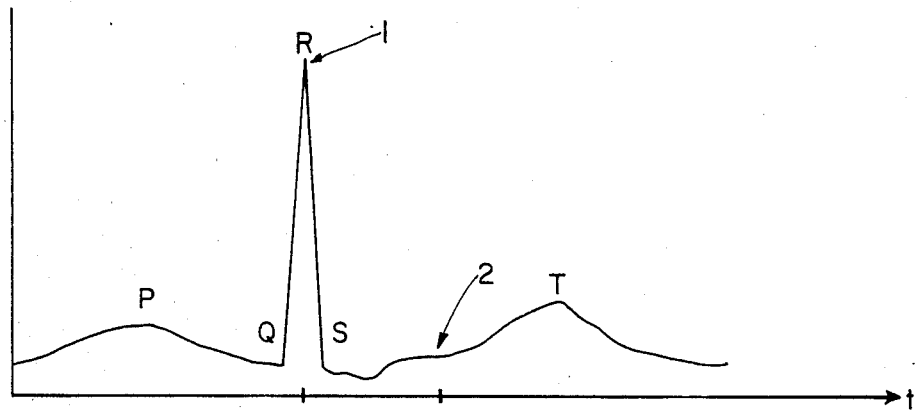
FIG. 1 shows the EKG voltages as a function of time for normal heartbeat.

Referring to FIG. 1, the terms P, Q, R, S, and T of the wave function are conventional in medicine. The steepest rise occurs at the leading edge of the QRS peak (FIG. 1). Point 2 shows a danger-free trigger time in the S-T interval of the patient's heartbeat cycle for applying shock waves. The EKG is recorded in known manner and a trigger pulse is obtained in known manner from the leading edge of the QRS peak and fed into a delay system. This system is adjustable within the range from 0 to 1000 msec and, depending on the time preselected by a physician (distance 1-2), delivers a trigger pulse to the spark gap, which is ignited and then generates a shock wave.

Figure 2:
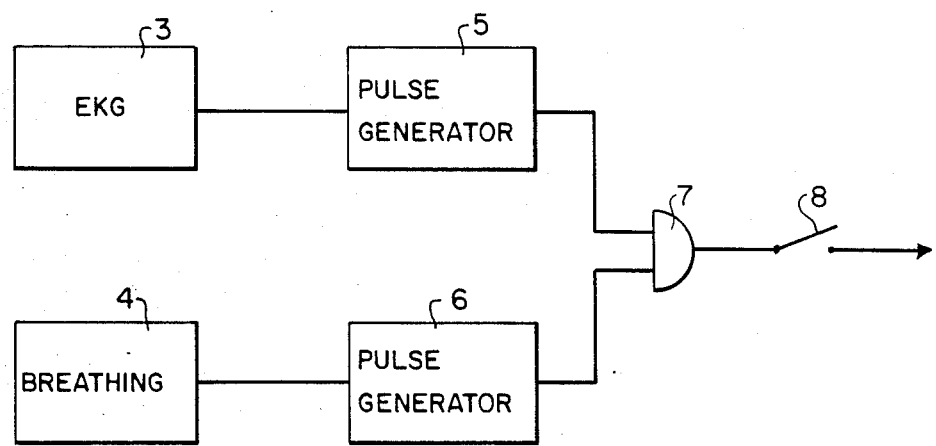
FIG. 2 is a block diagram of an instrument with further automation by taking into account a second body function, in this case breathing.

Referring to FIG. 2, two test-signal pick ups, pick up 3 for the EKG, and pick up 4 (such as a spirometer or respirometer) for the breathing motion, feed their test values each to a pulse generator 5, 6. These generators can be so set that they will deliver a pulse for a specific phase of the test values, for instance 10 msec after the occurrence of the QRS peak or at the time of the breathing pause which follows exhalation. The pulse generators are connected to the input of an AND gate 7. The output of a gate 7 is fed through a manual switch 8 to the spark gap.

A trigger pulse therefore arrives at the spark gap only when:

(a) the physician keeps the switch closed,
(b) the breathing motion is null, and
(c) the QRS peak of the EKG has just occurred.

Figure 3:
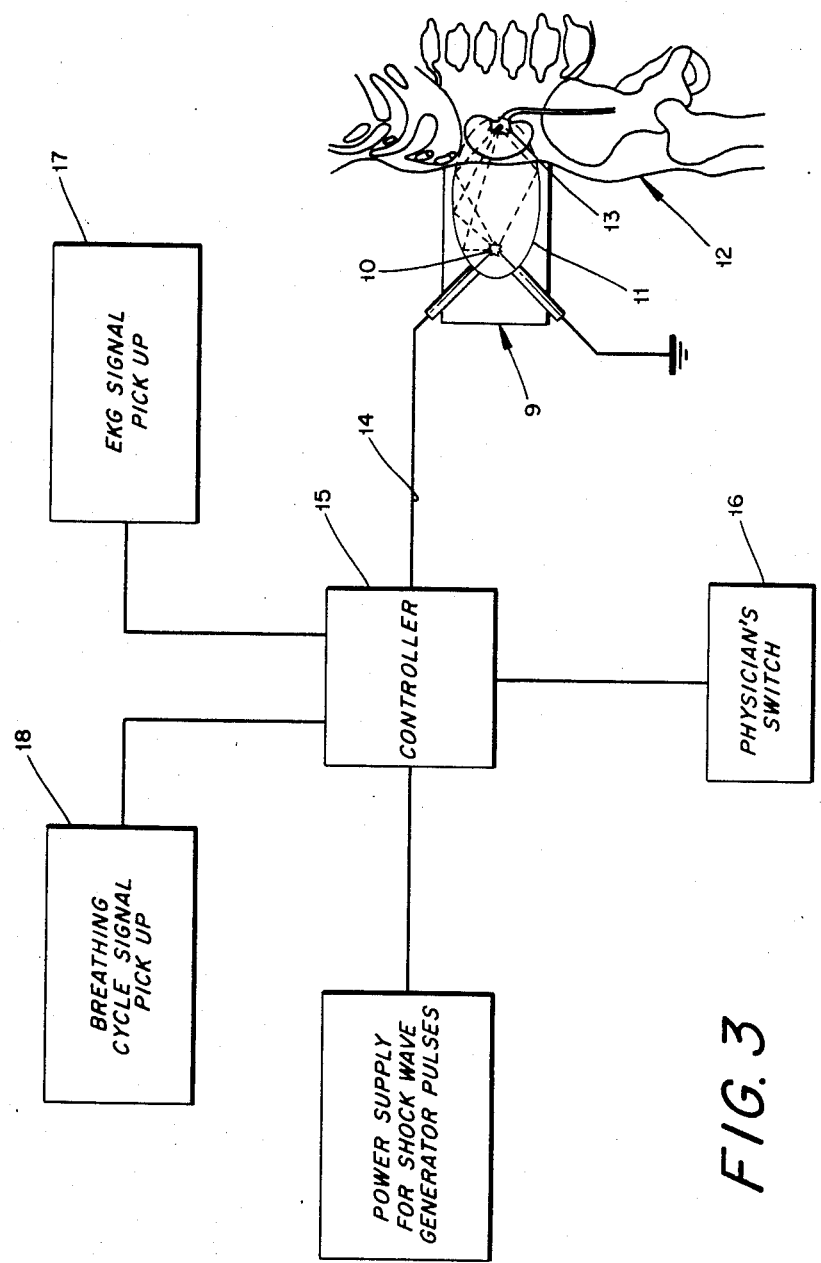
FIG. 3 is a diagrammatic representation of apparatus provided with a shock wave triggering system in accordance with the invention in which the matter to be treated by the shock waves is illustrated as a concretion or stone within a patient's kidney.

The overall system is depicted in FIG. 3. A shock wave generator 9, having a spark gap 10 for initiating shock waves and a curved reflector or waveguide 11 for focusing the shock waves, is shown diagrammatically in association with a schematic representation of a human patient 12. A concretion or stone 13 to be comminuted is shown as being located in a kidney, remote from the patient's heart and close enough to the lung area to be subject to movements as the patient breathes. The curved waveguide 11 is preferably of elliptical configuration, as described in the aforesaid U.S. Pat. No. 3,942,531, and it is intended that the spark gap 10 be at one focal point of the ellipse and the concretion 13 at the second focal point of the ellipse, so that the shock wave energy will be focused on the concretion 13 to comminute it efficiently.

Pulses of energy for firing the spark gap 10 of the shock wave generator 9 are passed to the shock wave generator by electrical conduit means 14 under control of means 15 operatively connected to and governed by various control inputs which assure that the triggering of the shock waves will not occur at the wrong moments as already explained above. That is, protection against extrasystole stimulation is provided by preventing passage of a pulse to the generator means except at times when both the physician has activated switch means 16 and the EKG signal pickup means 17 has provided an indication that a safe zone has been reached in the heartbeat cycle. Protection against focusing problems stemming from concretion movements during breathing is provided when pulse delivery is permitted only when the physician has activated his switch and the breathing cycle signal pickup means 18 has provided an indication that a selected portion of the breathing cycle has been reached.

Further body functions may be taken into account by further parallel signal channels, by the rapidly succeeding triggering of several shock waves by rapidly succeeding trigger pulses within one period, and by extracting the trigger pulse only from every second, third, etc. extreme value.

It will be obvious to those skilled in the art that many modifications may be made within the scope of the present invention without departing from the spirit thereof, and the invention includes all such modifications.

What we claim is:

1. In an apparatus for comminuting a concretion located at a place within the body of a patient remote from the patient's heart, such as within a kidney, by focusing shock waves from a shock wave generator means located outside the patient's body so that such waves pass through body tissue to the concretion to comminute such concretion, said apparatus including means for passing pulses of energy to said generator means for generating shock waves, an improved shock wave triggering system for use during the treatment of patients who might be subject to extrasystole stimulation, said triggering system comprising EKG signal pick up means adapted to respond to the patient's heartbeat cycle, means operatively connected to said EKG signal pick up means and to said means for passing pulses of energy to said generator means for enabling generation of a shock wave only during a safe zone in the S-T interval of the patient's heartbeat cycle, and manually operable physician's switch means operatively connected to said means for passing pulses of energy to said generator means for preventing the passage of a pulse to said generator means except when the physician has activated said switch means, so that a shock wave can be generated only at a time when both the physician's switch means has been activated and said safe zone has been reached in the heartbeat cycle.

2. The subject matter of claim 1 wherein said means connected to said EKG signal pick up means detects the R spike of the heartbeat cycle and wherein delay means is operative for an interval after the detection of said R spike to delay enabling of the generation of a shock wave until during the S-T interval of the patient's heartbeat cycle.

3. The subject matter of claim 2 wherein said delay means is adjustable so that said interval may be regulated.

4. The subject matter of claim 1 wherein said triggering system also includes means responsive to the patient's breathing cycle for enabling generation of a shock wave only during a selected portion of the patient's breathing cycle.

5. In a method of comminuting a concretion located at a place within the body of a patient remote from the patient's heart, such as within a kidney, by focusing shock waves from a shock wave generator located outside the patient's body so that such waves pass through body tissue to the concretion to comminute such concretion, the improvement comprising triggering generation of said shock waves only during time intervals within the patient's heartbeat cycle when the heart is not subject to stimulation into an extrasystole, by monitoring the patient's heartbeat cycle and preventing generation of a shock wave except at a time within the S-T interval of the heart cycle.

6. In an apparatus for comminuting a concretion, located at a place within the body of a patient such that the concretion is subject to movements as the patient breathes, by focusing shock waves from a shock wave generator means located outside the patient's body so that such waves pass through body tissue to the concretion to comminute such concretion, said apparatus including means for passing pulses of energy to said generator means for generating shock waves, an improved shock wave triggering system for controlling the passage of pulses of energy to said shock wave generator means so that a shock wave can be generated only during a selected portion of the patient's breathing cycle, said triggering system comprising signal pickup means adapted to respond to the patient's breathing cycle, means operatively connected to said signal pick up means and to said means for passing pulses of energy to said generator means for enabling generation of a shock wave only during the selected portion of the patient's breathing cycle, and manually operable physician's switch means operatively connected to said means for passing pulses of energy to said generator means for preventing the passage of a pulse to said generator means except when the physician has activated said switch means, so that a shock wave can be generated only at a time when both the physician's switch means has been activated and the concretion has reached a selected part of its path of movement in response to the breathing motion of the patient.

7. The subject matter of claim 6 wherein said signal pick up means includes a spirometer and wherein generation of a shock wave is enabled only during the portion of the breathing cycle which follows exhalation.

8. In a method of comminuting a concretion, located at a place within the body of a patient such that the concretion is subject to movements as the patient breathes, by focusing shock waves from a shock wave generator located outside the patient's body so that such waves pass through body tissue to the concretion to comminute such concretion, the improvement comprising triggering generation of shock waves only during time intervals within the patient's breathing cycle when the concretion has reached a selected part of its path of movement in response to the breathing motion of the patient, by monitoring the patient's breathing cycle and preventing generation of a shock wave except at a time within a selected part of the breathing cycle.

* * * * *